United States Patent [19]

Nakano et al.

[11] Patent Number: 4,740,641

[45] Date of Patent: Apr. 26, 1988

[54] PRODUCING A HALOGENATED BENZENE DERIVATIVE USING ZEOLITE CATALYST TREATED WITH ALKALI SOLUTION OF PH 11 OR MORE

[75] Inventors: Masao Nakano; Kazuhiko Sekizawa; Satoshi Fujii; Yukihiro Tsutsumi, all of Yamaguchi, Japan

[73] Assignee: Tosoh Corporation, Yamaguchi, Japan

[21] Appl. No.: 927,480

[22] Filed: Nov. 6, 1986

[30] Foreign Application Priority Data

Nov. 6, 1985 [JP] Japan .................................. 60-247117

[51] Int. Cl.$^4$ ............................................. C07C 17/12
[52] U.S. Cl. ..................................... 570/208; 570/147; 570/206
[58] Field of Search ................. 570/147, 206, 208, 207

[56] References Cited

U.S. PATENT DOCUMENTS 4,448,891  5/1984  Cohen ................................. 502/66

FOREIGN PATENT DOCUMENTS

| 0112722 | 7/1984 | European Pat. Off. | |
| 118851 | 9/1984 | European Pat. Off. | 570/208 |
| 154236 | 9/1985 | European Pat. Off. | 570/206 |
| 171265 | 2/1986 | European Pat. Off. | 570/208 |
| 224645 | 11/1985 | Japan | 570/206 |

Primary Examiner—J. E. Evans
Attorney, Agent, or Firm—Sughrue, Mion, Zinn, Macpeak, and Seas

[57] ABSTRACT

A p-substituted halobenzene derivative, which is very valuable in industry, can be obtained by halogenation of benzene and/or a benzene derivative in a liquid phase at a temperature of 0° to 200° C. at a higher selectivity and yield than in known processes, using, as a catalyst, an L type zeolite alkali-treated with an alkali solution of pH 11 or above at a temperature of 0° to 100° C. for 0.5 to 100 hours.

7 Claims, No Drawings

PRODUCING A HALOGENATED BENZENE DERIVATIVE USING ZEOLITE CATALYST TREATED WITH ALKALI SOLUTION OF PH 11 OR MORE

BACKGROUND OF THE INVENTION

1. Field of the Invention

The present invention relates to a process for producing a halogenated benzene derivative by halogenating benzene and/or a benzene derivative in a liquid phase. More particularly, the present invention relates to a process for selectively producing a p-substituted halobenzene derivative by halogenating benzene and/or a benzene derivative in a liquid phase using, as a catalyst, an alkali-treated L type zeolite.

2. Description of the Prior Art

Halogenated benzene derivatives are important raw materials or intermediates in various fields such as medicines, agricultural chemicals and organic synthesis chemistry. They are ordinarily produced by halogenating benzene and/or a benzene derivative in a liquid phase using, as a catalyst, a Lewis acid such as ferric chloride, antimony chloride or the like. For instance, dichlorobenzene (hereinafter abbreviated to DCB) is produced by blowing chlorine gas into benzene or monochlorobenzene (hereinafter abbreviated to MCB) in the presence of ferric chloride.

As is well known, in the production of a disubstituted benzene derivative by liquid phase halogenation of a mono-substituted benzene derivative, three isomers, namely, a 1,2-di-substituted benzene derivative (an o-isomer), a 1,3-di-substituted benzene derivative (an m-isomer) and a 1,4-di-substituted benzene derivative (a p-isomer) are formed as products, and the proportions of these isomers vary depending upon the kind of substituent possessed by the mono-substituted benzene derivative, the kind of catalyst used, etc. For instance, in the production of DCB by liquid phase chlorination of MCB in the presence of ferric chloride, the following three isomers are formed in the following proportions.

o-Dichlorobenzene: 30 to 40%
m-Dichlorobenzene: 0 to 5%
p-Dichlorobenzene: 60 to 70%

In the three kinds of isomers of di-substituted halobenzene derivatives, p-substituted halobenzene derivatives are most important industrially and are in greatest demand. Hence, a number of processes have hitherto been proposed for the selective production of p-substituted halobenzene derivatives.

These prior arts include processes for selectively producing a p-substituted halobenzene derivative by halogenating benzene and/or a benzene derivative using a zeolite as a catalyst. For instance, "Journal of Catalysis" 60, 110 (1979) describes the use of zeolite as a catalyst for bromination of halogenated benzene. In this literature, it is indicated that a p-substituted bromobenzene derivative can be produced selectively by using, as a bromination catalyst, various ion exchange zeolites, namely, X type and Y type zeolites. Further, "Tetrahedron Letters" 21, 3809 (1980) describes the chlorination of benzene using various catalysts such as ZSM-5, ZSM-11, mordenite, L type zeolite and Y type zeolite. It is indicated in the literature that L type zeolite, in particular, can produce p-dichlorobenzene at a high selectivity. Furthermore, for example, Japanese patent public disclosure (Laid-Open Publication) Nos. 130227/1984, 144722/1984 and 163329/1984 disclose processes for halogenating benzene or an alkylbenzene using L type zeolite or Y type zeolite as a catalyst.

It is obvious from the prior arts that in halogenation of benzene and/or a benzene derivative, processes using a zeolite catalyst can produce a p-substituted halobenzene derivative at a higher selectivity than conventional processes using a Lewis acid catalyst (e.g., ferric chloride). However, the selectivity of a p-substituted halobenzene derivative in said prior art processes using a zeolite catalyst is still insufficient from an industrial viewpoint. Accordingly, it is desired to develop a process for producing a p-substituted halobenzene derivative at an enhanced selectivity.

On the other hand, with respect to the alkali treatment of L type zeolite, Japanese patent public disclosure (Laid-Open Publication) No. 80333/1984, discloses a process for reforming a hydrocarbon using, as a catalyst, a noble metal (e.g., platinum) supported by an alkali-treated L type zeolite carrier. It is indicated in the literature that the use of said alkali treated L type zeolite as a catalyst carrier in the gas phase aromatization of aliphatic hydrocarbons can improve the life of the catalyst used.

However, it is impossible to predict from the above literature that the use of said alkali-treated L type zeolite catalyst for liquid phase halogenation of benzene and/or a benzene derivative can enhance the selectivity of a p-substituted halobenzene derivative.

SUMMARY OF THE INVENTION

It is therefore an object of the present invention to provide a p-substituted halobenzene derivative by halogenating benzene and/or a benzene derivative in a liquid phase at a high selectivity, characterized by using, as a catalyst, a L type zeolite alkali-treated with an alkali solution of pH 11 or above, preferably pH 13 or above.

Other objects and advantages of the present invention will become apparent to those skilled in the art from the following description and disclosure.

DETAILED DESCRIPTION OF THE PREFERRED EMBODIMENT

The present invention uses a zeolite catalyst. Zeolite is commonly known as a crystalline aluminosilicate. It has a structure consisting of $SiO_4$ tetrahedrons and $AlO_4$ tetrahedrons. Various types of zeolites are known depending upon the type of bonding of these tetrahedrons. Each zeolite has a different crystal structure and can be identified by means of X-ray diffractometry (powder method). The zeolite used in the present invention as a catalyst is L type zeolite. The measurement results for L type zeolite by X-ray diffractometry using a copper $K\alpha$ doublet are shown in Table 1.

TABLE 1

| Diffraction angle $2\theta(°)$ ($\pm 0.2°$) | Lattice distance $d(\text{Å})$ ($\pm 0.1$ Å) | Relative intensity $I/I_o$ |
| --- | --- | --- |
| 5.6 | 15.8 | 100 |
| 11.2 | 7.89 | 5 to 40 |
| 11.8 | 7.49 | 10 to 100 |
| 14.8 | 5.98 | 10 to 100 |
| 15.3 | 5.79 | 10 to 40 |
| 19.4 | 4.57 | 30 to 80 |
| 20.2 | 4.39 | 10 to 70 |
| 20.5 | 4.33 | 10 to 70 |
| 22.7 | 3.91 | 30 to 120 |
| 23.4 | 3.80 | 5 to 40 |
| 24.3 | 3.66 | 10 to 70 |

TABLE 1-continued

| Diffraction angle 2θ(°) (±0.2°) | Lattice distance d(Å) (±0.1 Å) | Relative intensity I/I₀ |
|---|---|---|
| 25.6 | 3.48 | 20 to 80 |
| 27.2 | 3.28 | 10 to 60 |
| 28.0 | 3.18 | 30 to 120 |
| 29.1 | 3.07 | 20 to 80 |
| 29.8 | 3.00 | 5 to 40 |
| 30.8 | 2.91 | 20 to 80 |
| 33.8 | 2.65 | 10 to 70 |
| 34.2 | 2.62 | 5 to 50 |

L type zeolite is one kind of synthetic zeolite and can be synthesize according to a known process [e.g. Japanese patent public disclosure (Laid-Open Publication) No. 73421/1984, Japanese patent publication Nos. 35604/1971 and 3675/1961]. L type zeolite typically has the following formula when expressed in the mole ratio of oxides:

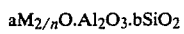

$$aM_{2/n}O \cdot Al_2O_3 \cdot bSiO_2$$

(wherein a=1.0±0.3, b=4 to 8, and n is the valency of M, a cation). L type zeolite as synthesized contains Na ion and/or K ion as the cation M.

In the present invention, the cation contained in L type zeolite has no restriction. Therefore, a synthesized L type zeolite which contains Na ion and/or K ion can be used as it is. However, an L type zeolite obtained by exchanging Na ion and/or K ion into other cation(s) can also be used, if necessary. This ion-exchange treatment may be effected by an aqueous solution containing a desired cation, according to a known method.

The L type zeolite used in the present invention as a catalyst must be alkali-treated. This alkali treatment involves soaking an L type zeolite in an alkali solution. The alkali treatment of L type zeolite is conducted using an alkali solution of pH 11 or above, preferably pH 13 or above. The upper limit of the pH of the alkali solution is not restricted to any particular value. However, if the pH of the alkali solution is high, the treatment temperature is high and the treatment time is long, so that the crystalline structure of the L type zeolite may sometimes be destroyed, whereby the alkali solution is preferably pH 15 or below. There is no particular restriction on the alkali employed so long as its alkali solution has a pH of 11 or above. The alkali can be an inorganic compound or an organic compound. As the inorganic alkali compound, mention can be made, for example, of compounds containing (a) at least one cation selected from lithium, sodium, potassium, rubidium, cesium, beryllium, magnesium, calcium, strontium and barium and (b) at least one anion selected from hydroxyl group, carbonate anion, borate anion and phosphate anion. Ammonia and so forth can also be mentioned. As the organic alkali compound, mention can be made, for example, of amine compounds such as methylamine and the like. Preferable alkalis are sodium hydroxide, potassium hydroxide, rubidium hydroxide, cesium hydroxide and their mixture.

There is no particular restriction on the solvent used in the alkali solution so long as it can dissolve the above alkalis and the resulting solution has a pH of 11 or above. Ordinarily, water is preferably used, but other solvents such as an alcohol or an alcohol-water mixture can also be used.

There is no particular restriction on the amount of alkali solution used for the alkali treatment of the L type zeolite so long as the amount is enough to suspend the zeolite in the alkali solution. The amount is ordinarily 5 to 500 ml per g of zeolite, preferably 10 to 100 ml per g of zeolite.

The effect of the alkali treatment differs according to the pH of the alkali solution, the treatment temperature and the treatment time. The effect is small when the pH of the alkali solution is low, the treatment temperature is low and the treatment time is short. If the pH of the alkali solution is high, the treatment temperature is too high and the treatment time is too long so that, the crystalline structure of the L type zeolite may be destroyed; therefore, such conditions are undesirable. Since the pH of the alkali solution, the treatment temperature and the treatment time are closely connected in the alkali treatment of L type zeolite, it is difficult to specify the alkali treatment conditions within certain limits. However, when the pH of the alkali solution is within the above-mentioned range, the treatment temperature is generally selected to be between 0° C. and 100° C., preferably between 20° C. and 90° C., and the treatment time is generally selected to be between 0.5 hour and 100 hours, preferably between 3 hours and 50 hours.

The alkali treatment is ordinarily effected by stirring a slurry comprising an alkali solution and an L type zeolite. It may alternatively be conducted with the slurry being allowed to stand.

After the alkali treatment, the L type zeolite is separated from the alkali solution by filtration or the like. Then, the separated zeolite is washed with the solvent used in the alkali solution until the pH of the washings becomes 8 or below. After washing, the zeolite is dried for 1 to 24 hours at 80° to 150° C. to obtain an alkali-treated L type zeolite.

In the present invention, the shape of the catalyst is not particularly restricted. Ordinarily, the catalyst is used after being molded into a desired shape but it may be used in a powder form. Molding can be conducted according to an ordinary method such as extrusion molding, tablet molding, spray-drying granulating molding or the like. In molding, substances which are inert to the halogenation reaction can be added as a binder or as a molding aid in order to enhance the mechanical strength of the molding obtained. For example, substances such as silica, clay, graphite, stearic acid, starch, polyvinyl alcohol and the like can be added in an amount of 0 to 80% by weight, preferably 2 to 30% by weight.

The catalyst is then calcined before being used in liquid phase halogenation. The calcination is conducted for 1 to 10 hours at 300° to 700° C. in air.

In the present invention, the term "benzene derivative" means a compound in which a hydrogen atom of benzene is replaced by a substituent such as a halogen atom or an alkyl group. The compounds are, for example, halogenated benzenes and alkylated benzenes and specifically are monofluorobenzene, MCB, monobromobenzene, monoiodobenzene, toluene, ethylbenzene, etc. The halogenating agent can be an elementary halogen such as chlorine, bromine, iodine or the like.

In the present invention, there is no particular restriction on the kind of reactor used, the reaction method or the reaction conditions, so long as benzene and/or a benzene derivative contacts the catalyst in a liquid phase. For example, the reactor can be of the batch-wise, semibatch-wise or continuous type. The catalyst can be used, for example, in the form of a fixed bed or a suspended bed. The reaction may be conducted in the presence of a solvent which is inert to the halogenation reaction, such as carbon tetrachloride or the like. When such a solvent is used, the concentration of benzene and/or a benzene derivative can be 5 to 99% by weight, preferably 20 to 99% by weight. When the concentration is below 5% by weight, the chance of contact of the raw material with the catalyst is reduced and sufficient conversion cannot be obtained. When a halogenating agent is supplied continuously, the agent can be accompanied by an inert gas such as nitrogen, helium, carbon dioxide or the like. When such an accompanying gas is used, the concentration of halogenating agent can be 5 to 99% by volume, preferably 20 to 99% by volume.

When a batch-wise or semi-batch-wise reactor is used, the catalyst is used in most cases in a suspended bed in a solvent. The amount of catalyst can be 0.001 to 1 kg per liter of reaction solution, preferably 0.005 to 0.1 kg per liter of reaction solution. When the amount is less than 0.001 kg/liter, the load on the catalyst is too high and sufficient conversion cannot be obtained. When the amount is more than 1 kg/liter, the effect of catalyst increase is small. When the halogenating agent is supplied continuously, the amount of halogenating agent supplied can be expressed as the amount of halogenating agent per unit time per unit weight of zeolite. It can be 1 to 1,500 mole per hour per kg of catalyst, preferably 10 to 800 mole per hour per kg of catalyst. When the amount of halogenating agent is less than 1 mole per hour per kg of catalyst, a sufficient production rate of halogenated benzene cannot be obtained. When the amount exceeds 1,500 mole per hour per kg of catalyst, the amount of unreacted halogenating agent increases, which is uneconomical.

When a continuous reactor is used, the amount of liquid raw material supplied can be expressed as the amount of liquid raw material per unit time per unit weight of zeolite and can be 0.5 to 300 liters per hour per kg of catalyst, preferably 2 to 100 liters per hour per kg of catalyst. The other reaction conditions are the same as those employed when a batch-wise or semi-batch-wise reactor is used.

In the present invention, there is no particular restriction on the reaction temperature and the reaction pressure so long as benzene and/or a benzene derivative is in a liquid phase. When the reaction temperature is higher than the boiling point of benzene and/or a benzene derivative, halogenation in a liquid phase can be effected by increasing the reaction pressure. The reaction temperature is preferably 0° to 200° C., more preferably 20° to 150° C.. When the temperature is lower than 0° C., a sufficient reaction rate cannot be obtained. When the temperature exceeds 200° C., the selectivity of a p-substituted halobenzene derivative is low.

According to the present invention, a p-substituted halobenzene derivative which is very valuable in industry can be obtained by halogenation of benzene and/or a benzene derivative in a liquid phase, at a higher selectivity and yield than in known processes with the same activity (rate of conversion). In the case of the production of substituted halobenzene derivatives, isomerization reaction and recycling use of o-isomers are not usually conducted, because the isomerization reaction itself is very difficult. In addition, m-isomers are largely produced in isomerization of o-isomers due to equilibrium. Consequently, even when the selectivity of p-isomers is improved a little, the amount of by-product o-isomers and the like, which are less valuable in industry, is reduced significantly, whereby p-isomers are easily separated and purified and the production cost of p-isomers is reduced. For example, if the selectivity of p-isomers is improved from 85% to 86%, the amounts of the by-product o-isomers and the like are reduced by 7%. Therefore, the present invention has a very high industrial significance.

EXAMPLES

The present invention will be explained in more detail below by way of Examples. However, the present invention is in no way restricted to these Examples. The terms "conversion", "selectivity" and "yield" used in the Examples refer to values calculated by the following formulations, respectively.

$$\text{Conversion (\%)} = \frac{\text{amount (mole) of benzene and/or benzene derivative fed} - \text{amount (mole) of benzene and/or benzene derivative unreacted}}{\text{amount (mole) of benzene and/or benzene derivative fed}} \times 100$$

$$\text{Selectivity (\%)} = \frac{\text{amount (mole) of desired product produced}}{\text{total amount (mole) of all products produced}} \times 100$$

$$\text{Yield (\%)} = \frac{\text{Conversion (\%)} \times \text{Selectivity (\%)}}{100}$$

EXAMPLE 1

An L type zeolite was synthesized hydrothemally according to the method of Japanese patent public disclosure (Laid-Open Publication) No. 73421/1984. The resulting slurry was filtered and the solid collected was water-washed thoroughly and then dried for 15 hours at 110° C. This solid had the following formulation when expressed in terms of the mole ratio of oxides.

$$0.01Na_2O.0.99K_2O.Al_2O_3.6.2SiO_2$$

X-ray diffractometry (powder method) by copper K$\alpha$ doublet for the solid gave a diffraction pattern as shown in Table 2, and the solid was confirmed to be an L type zeolite.

TABLE 2

| Diffraction angle $2\theta(°)$ ($\pm 0.2°$) | Lattice distance $d(Å)$ ($\pm 0.1$ Å) | Relative intensity $I/I_o$ |
|---|---|---|
| 5.6 | 15.8 | 100 |
| 11.2 | 7.89 | 6 |
| 11.8 | 7.49 | 30 |
| 14.8 | 5.98 | 36 |
| 15.3 | 5.79 | 19 |
| 19.4 | 4.57 | 60 |
| 20.2 | 4.39 | 19 |
| 20.5 | 4.33 | 19 |
| 22.7 | 3.91 | 69 |
| 23.4 | 3.80 | 9 |
| 24.3 | 3.66 | 41 |
| 25.6 | 3.48 | 57 |
| 27.2 | 3.28 | 32 |
| 28.0 | 3.18 | 72 |
| 29.1 | 3.07 | 53 |
| 29.8 | 3.00 | 9 |
| 30.8 | 2.91 | 61 |
| 33.8 | 2.65 | 29 |

TABLE 2-continued

| Diffraction angle 2θ(°) (±0.2°) | Lattice distance d(Å) (±0.1 Å) | Relative intensity I/I_o |
| --- | --- | --- |
| 34.2 | 2.62 | 20 |

Fifteen grams of the L type zeolite obtained above was subjected to an alkali treatment by stirring the zeolite with 500 ml of an aqueous sodium hydroxide solution of pH 14.3 for 10 hours at 90° C. The resulting slurry was filtered and the solid collected was washed by water until the pH of the washings became pH 8 or below. Then, the solid was dried for 15 hours at 110° C., after which it was calcinated for 3 hours at 540° C. in an air current. Using the resulting solid as a catalyst, liquid phase chlorination of MCB was conducted.

The chlorination was conducted using an ordinary semi-batch-wise reactor. A Pyrex reactor (inner diameter: 40 mm, height: 100 mm) having an internal volume of about 100 ml and equipped with a gas-introducing tube and a condenser was filled with 40 g of MCB. Therein was suspended 1 g of an alkali-treated L type zeolite. With the reactor contents being thoroughly stirred with a magnetic stirrer, a 50/50 mixture of chlorine gas and nitrogen gas was blown into the reactor at a rate of 30 ml/min (for Cl2). The reaction temperature was controlled at 100° C. by heating the reactor with an oil bath. After 3 hours has passed from the start of gas mixture blowing, the products formed were analyzed by means of gas chromatography. The results are shown in Table 3.

EXAMPLES 2 and 3

Fifteen grams of the L type zeolite synthesized in Example 1 was subjected to an alkali treatment by stirring with 500 ml of an aqueous sodium hydroxide solution of pH 14.3 for 10 hours at 50° C. or by stirring with an aqueous sodium hydroxide solution of pH 14.0 for 10 hours at 90° C. The resulting alkali-treated zeolites were each subjected to a post-treatment. Using the catalysts thus obtained, liquid phase chlorination of MCB was effected in the same manner as in Example 1. The results of reaction after 3 hours from the start of gas mixture blowing are shown in Table 3.

EXAMPLES 4 and 8

Fifteen grams of the L type zeolite synthesized in Example 1 was subjected to an alkali treatment by stirring with 500 ml of an aqueous potassium hydroxide solution of pH 11.0, 13.2, 14.0, 14.3 or 14.6 for 5 hours at 90° C.. The resulting alkali-treated zeolites were each subjected to a post-treatment. Using the catalysts thus obtained, liquid phase chlorination of MCB was effected in the same manner as in Example 1. The results of reaction after 3 hours from the start of gas mixture blowing are shown in Table 3.

COMPARATIVE EXAMPLE 1

The L type zeolite synthesized in Example 1 was calcinated for 3 hours at 540° C. in an air current, without being subjected to any alkali treatment. Using this calcinated zeolite as a catalyst, chlorination of MCB was effected in the same manner as in Example 1. The results of reaction after 3 hours from the start of gas mixture blowing are shown in Table 3.

COMPARATIVE EXAMPLE 2

Five grams of the L type zeolite synthesized in Example 1 and 200 ml of an aqueous sodium hydroxide solution of pH 14.8 were fed into an autoclave, and the alkali treatment of the zeolite was effected for 110 hours at 120° C. with stirring. Using the catalysts thus obtained, chlorination of MCB was effected in the same manner as in Example 1. The results of reaction after 3 hours from the start of gas mixture blowing are shown in Table 3.

The alkali-treated L type zeolite used in this Comparative Example was subjected to X-ray diffractometry (powder method) by copper Kα doublet, where the diffraction pattern of Table 2 was not to be observed. This confirmed that the alkali treatment of this Comparative Example destroyed the crystalline structure of L type zeolite.

COMPARATIVE EXAMPLE 3

Fifteen grams of the L type zeolite synthesized in Example 1 was subjected to an alkali treatment by stirring with 500 ml of an aqueous potassium hydroxide solution of pH 10.0 for 5 hours at 90° C. Then, the alkali-treated zeolite was subjected to a post-treatment. Using the resulting zeolite as a catalysts, liquid phase chlorination of MCB was effected in the same manner as in Example 1. The results of reaction after 3 hours from the start of gas mixture blowing are shown in Table 3.

TABLE 3

| | Conditions of alkali treatment | | | | Conversion (%) | Selectivity (%) | | | Yield (%) |
| | Alkali | pH | Temp. (°C.) | Time (hours) | | PDCB | ODCB | Others*[1] | PDCB |
| --- | --- | --- | --- | --- | --- | --- | --- | --- | --- |
| Example | | | | | | | | | |
| 1 | NaOH | 14.3 | 90 | 10 | 67.1 | 92.1 | 7.2 | 0.7 | 61.8 |
| 2 | NaOH | 14.3 | 50 | 10 | 67.3 | 89.3 | 9.8 | 0.9 | 60.1 |
| 3 | NaOH | 14.0 | 90 | 10 | 67.2 | 91.0 | 8.2 | 0.8 | 61.2 |
| 4 | KOH | 11.0 | 90 | 5 | 67.9 | 88.3 | 10.7 | 1.0 | 60.0 |
| 5 | KOH | 13.2 | 90 | 5 | 67.7 | 89.0 | 10.1 | 0.9 | 60.3 |
| 6 | KOH | 14.0 | 90 | 5 | 67.8 | 89.3 | 9.7 | 1.0 | 60.6 |
| 7 | KOH | 14.3 | 90 | 5 | 67.1 | 89.9 | 9.1 | 1.0 | 60.3 |
| 8 | KOH | 14.6 | 90 | 5 | 67.6 | 91.3 | 7.7 | 1.0 | 61.7 |
| comp. Example | | | | | | | | | |
| 1 | — | — | — | — | 67.1 | 87.7 | 11.4 | 0.9 | 58.9 |
| 2 | NaOH | 14.8 | 120 | 110 | 12.9 | 69.3 | 15.3 | 15.4 | 8.94 |
| 3 | KOH | 10.0 | 90 | 5 | 67.4 | 87.6 | 11.4 | 1.0 | 59.0 |

*[1]m-Dichlorobenzene (MDCB), trichlorobenzene, etc.

EXAMPLE 9

Using, as a catalyst, the alkali-treated L type zeolite prepared in Example 1, liquid phase chlorination of toluene was effected in the same manner as in Example 1 except that the MCB used in Example 1 was replaced by toluene. The results of reaction after 3 hours from the start of gas mixture blowing are shown in Table 4.

COMPARATIVE EXAMPLE 4

Liquid phase chlorination of toluene was conducted in the same manner as in Example 9 except that the L type zeolite used in Comparative Example 1 was used as a catalyst. The results of reaction after 3 hours from the start of gas mixture blowing are shown in Table 4.

TABLE 4

| | Conversion (%) | Selectivity (%)[1] | | | Yield (%) PCT |
|---|---|---|---|---|---|
| | | PCT | OCT | Others | |
| Example 9 | 55.3 | 64.5 | 29.8 | 5.7 | 35.7 |
| Comp. Example 4 | 55.9 | 61.1 | 33.2 | 5.7 | 34.2 |

[1]PCT: p-chlorotoluene  OCT: o-chlorotoluene  Others: m-chlorotoluene, dichlorotoluene, etc.

What is claimed is:

1. A process for producing a p-substituted halogenated benzene derivative, which comprises halogenating benzene and/or a benzene derivative in the liquid phase using as a catalyst an L type zeolite alkali-treated with an alkali solution of a pH of 11 or above, wherein the benzene derivative is one where a hydrogen atom of benzene has been replaced with a substitutent selected from the group consisting of a halogen atom and an alkyl group, and wherein the process is conducted at a temperature of 0 to 200° C.

2. The process according to claim 1, wherein the pH of the alkali solution is 13 or above.

3. The process according to claim 1, wherein the alkali treatment is conducted at the temperature of 0 to 100° C. for 0.5 to 100 hours.

4. The process according to claim 2, wherein the alkali treatment is conducted at the temperature of 0 to 100° C. for 0.5 to 100 hours.

5. The process according to claim 1, wherein the alkali treatment is conducted at the temperature of 20 to 90° C. for 3 to 50 hours.

6. The process according to claim 2, wherein the alkali treatment is conducted at the temperature of 20 to 90° C. for 3 to 50 hours.

7. The process according to claim 1, wherein the pH of the alkali solution is from 11 to 15.

* * * * *